United States Patent

Wos et al.

[11] Patent Number: 6,066,751
[45] Date of Patent: May 23, 2000

[54] PROCESS FOR MAKING EPOXIDE INTERMEDIATES

[75] Inventors: John August Wos, Cincinnati; Jack Snyder Amburgey, Jr., Loveland; Mitchell Anthony deLong, West Chester; Yili Wang, Mason, all of Ohio; Haiyan George Dai, Drexel Hill, Pa.; Biswanath De, Cincinnati, Ohio

[73] Assignee: The Procter & Gamble Company, Cincinnati, Ohio

[21] Appl. No.: 09/148,539

[22] Filed: Sep. 4, 1998

Related U.S. Application Data

[60] Provisional application No. 60/058,254, Sep. 9, 1997.

[51] Int. Cl.[7] ................................................... C07D 301/14
[52] U.S. Cl. .......................... 549/525; 549/561; 560/121; 562/503
[58] Field of Search ..................................... 549/525, 561; 560/121; 562/503

[56] References Cited

U.S. PATENT DOCUMENTS

| | | | |
|---|---|---|---|
| 3,435,053 | 3/1969 | Beal et al. | 260/345.2 |
| 3,505,386 | 4/1970 | Babcock et al. | 260/468 |
| 3,776,938 | 12/1973 | Bergstrom et al. | 260/468 D |

*Primary Examiner*—Ba K. Trinh
*Attorney, Agent, or Firm*—James C. Kellerman; Carl J. Roof

[57] ABSTRACT

It has been surprisingly discovered that the disadvantages of the lengthy literature procedures to synthesize 13,14-dihydro prostaglandin A, E, and F derivatives can be overcome using a novel Methyl 7-(2-hydroxy-5-(2-(2-oxiranyl)ethyl)-4-(1,1,2,2 tetramethyl-1-silapropoxy)cyclopentyl) heptanoate intermediate, which can be synthesized from commercially available Methyl 7-[3-(R)-hydroxy-5-oxo-1-cyclopent-1-yl] heptanoate. This novel intermediate can be coupled with oxygen, carbon, sulfur, and nitrogen nucleophiles, in the presence of a base or a Lewis acid, in a ring-opening process to provide 13,14-dihydro prostaglandin A, E, and F derivatives.

14 Claims, No Drawings

PROCESS FOR MAKING EPOXIDE INTERMEDIATES

CROSS REFERENCE

This application claims priority under Title 35, United States Code 119(e) from Provisional Application Ser. No. 60/058,254, filed Sep. 9, 1997.

TECHNICAL FIELD

The present invention describes a process for making a novel epoxide intermediate useful for making 13,14-dihydro prostaglandin A, E and F derivatives.

BACKGROUND OF THE INVENTION

The present invention describes a novel process for making a novel epoxide intermediate useful for making 13,14-dihydro prostaglandin A, E and F derivatives. Naturally occurring prostaglandins (PGA, PGB, PGD, PGE, PGF, and PGI) are C-20 unsaturated fatty acids. Prostaglandin A, E, and F derivatives are distinguishable as such by the substituents on the alicyclic ring. PGA derivatives are characterized by a ketone at $C_9$ and a double bond between $C_{10}$ and $C_{11}$. PGE derivatives are characterized by a ketone at $C_9$ and a hydroxyl at $C_{11}$. PGF derivatives are characterized by hydroxyl groups at both $C_9$ and at $C_{11}$.

Such derivatives are useful for the treatment of many medical disorders including, for example, ocular disorders, hypertension, fertility control, and osteoporosis. For example, the prostaglandin 13,14-dihydro $PGF_1\alpha$, disclosed in U.S. Pat. No. 3,776,938 (1973) by Bergstrom, S., and Sjovall, J. of the Kemiska Institutionen, Karolinska Institute, Stockholm 60, Sweden has a stimulatory effect on smooth muscle contraction as shown by test strips of guinea pig ileum, rabbit duodenum, or gerbil colon. Further information regarding the biological effects of 13,14-dihydro PGA, PGE and PGF derivatives are disclosed in the following references: U.S. Pat. No. 3,882,241 issued to Pharriss, G., May 6, 1975; G.B. U.S. Pat. No. 1,456,512 (1976) issued to Pfizer Inc., Bundy, G. L.; Lincoln, F. H., "Synthesis of 17-Phenyl-18,19,20-trinor prostaglandins I. The PG1 Series", *Prostaglandins* Vol. 9 (1975) pp. 1–4; CRC Handbook of Eicosanoids: Prostaglandins and Related Lipids Vol. 1, Chemical and Biochemical Aspects, Parts A & B, A. L. Willis, eds., CRC Press (1987); Liljebris, C.; et. al. "Derivatives of 17-Phenyl-18,19,20-trinorprostaglandin F2α Isopropyl Ester: Potential Antiglaucoma Agents", *Journal of Medicinal Chemistry* Vol. 38, (1995), pp. 289–304; Collins, P. W.; Djuric, S. W. "Synthesis of Therapeutically Useful Prostaglandin and Prostacyclin Analogs", *Chemical Reviews* 93 (1993), pp. 1533–1564.

In the art, 13,14 dihydro prostaglandin E derivatives have been synthesized according to several different methods. Such methods include those described in the following references: Corey et al., *J. Amer. Chem. Soc.* 1969, 91, p. 5675; Corey et al., *J. Amer. Chem. Soc.* 1970, 92, p. 397; Corey et al., *J. Amer. Chem. Soc.* 1970, 92, p. 2586; Corey, E. J. *Ann. N.Y. Acad. Sci.* 1971, 180, p. 24; Corey et al., *The Logic of Chemical Synthesis*, John Wiley & Sons: New York, 1989, p. 250–266.

To date, prostaglandin E derivatives have generally been assembled through the common Corey aldehyde intermediate via introduction of the omega side-chain through Wadsworth-Horner-Emmons phosphonate chemistry, reduction and protection of the $C_{15}$ position, introduction of the top chain via Wittig chemistry, oxidation of the $C_9$ position with Jones reagent, and finally, removal of the various protecting groups with the appropriate reagent(s).

Prostaglandins of the A series have generally been assembled from the PGE series by acid or base induced elimination of the C11 hydroxyl group. Methods for conversion of PGE derivatives to PGA derivatives include those described in the following references: Stork et al., *J. Amer. Chem. Soc.* 1976, 98, p. 1583; Stork et al., *J. Amer. Chem. Soc.* 1978, 100, p. 8272.

In the art, 13,14 dihydro prostaglandin F derivatives have been synthesized according to several different methods. Such methods include those described in the following references: G.B Patent No. 1,040,544 issued to A. C. Chapman; G.B. Patent No. 1,186,505 issued to the Upjohn Co.; U.S. Pat. No. 3,505,386 issued to Babcock, J. C., and Beal, P. F., III, Apr. 7, 1970, U.S. Pat. No. 3,435,053 issued to Beal, Lincoln, Jr., Portage, and Pike, Mar. 25, 1969; G.B. Patent No. 1,251,750 issued to the Upjohn Co.; Bundy, G. L.; Lincoln, F. H. "Synthesis of 17-Phenyl-18,19,20-trinorprostaglandins I. The $PG_1$ Series" *Prostaglandins*, Vol. 9 (1975), pp. 1–4.

To date, the synthesis of 13,14-dihydro prostaglandin F derivatives has involved either conversion of the 13,14-dihydro prostaglandin $E_1$ skeleton (see Sjovall, et. al., U.S. Pat. No. 3,776,938) via reduction of the carbonyl moiety at Cg (prostaglandin numbering) to the alcohol or by exhaustive hydrogenation of the preassembled $PGF_2\alpha$ skeleton (see for example: Bundy, G. L.; Lincoln, F. H. "Synthesis of 17-Phenyl-18,19,20-trinor prostaglandins I. The $PG_1$ Series" *Prostaglandins*, Vol. 9 (1975), pp. 1–4.) The prostaglandin $F_2\alpha$ skeleton is prepared in a variety of ways; generally from the condensation of the Corey aldehyde (see for example: Corey, E. J.; Weinshenker, N. M.; Schaaf, T. K.; Huber, W. "Stereo-Controlled Synthesis of Prostaglandins $F_{2\alpha}$ and $E_2$ (dl)" *J. Am. Chem. Soc.* 1969, 91(20), p.5675–5677] with the appropriate oxophosphonate, followed by reduction at $C_{15}$ (prostaglandin numbering)(see, for example: Noyori, R,; Tomino, I.; Yamada, M.; Nishizawa, M. "Synthetic Applications of the Enantioselective Reduction by Binaphthol-Modified Lithium Aluminum Hydride Reagents" *J. Amer. Chem. Soc.* 1984, 106, p. 6717–6725), reduction to the lactol and addition of the $C_1$–$C_7$ (prostaglandin numbering) sidechain (see, for example: G.B. Patent No. 1,456,512, complete specification published Nov. 24, 1976). For other methods to prepare the prostaglandin $F_2\alpha$ skeleton for conversion into the 13,14-dihydro prostaglandin F1α derivatives, see: Collins, P. W.; Djuric, S. W. "Synthesis of Therapeutically Useful Prostaglandin and Prostacyclin Analogs", *Chemical Reviews*, 93, (1993), pp.1533–1564.

Synthesis of 13,14-dihydro prostaglandin A, E, and F derivatives using the methods described above is somewhat lengthy and expensive. Thus, it would be desirable to have a method that is higher yielding, more economical, and that involves fewer steps for preparing 13,14-dihydro prostaglandin A, E, and F derivatives.

SUMMARY OF THE INVENTION

It has been surprisingly discovered that the disadvantages of the lengthy literature procedures to synthesize 13,14-dihydro prostaglandin A, E, and F derivatives can be overcome using a novel Methyl 7-(2-hydroxy-5-(2-(2-oxiranyl) ethyl)-4-(1,1,2,2 tetramethyl-1-silapropoxy)cyclopentyl) heptanoate intermediate, which can be synthesized from commercially available Methyl 7-[3-(R)-hydroxy-5-oxo-1-cyclopent-1-yl] heptanoate. This novel intermediate can be coupled with oxygen, carbon, sulfur, and nitrogen nucleophiles, in the presence of a base or a Lewis acid, in a ring-opening process to provide 13,14-dihydro prostaglandin A, E, and F derivatives.

DETAILED DESCRIPTION OF THE INVENTION

The present invention is directed to a process for making a novel Methyl 7-(2-hydroxy-5-(2-(2-oxiranyl)ethyl)-4-(1,1,2,2 tetramethyl-1-silapropoxy)cyclopentyl) heptanoate intermediate (the "epoxide intermediate"). This epoxide intermediate is useful for making 13,14-dihydro prostaglandin A, E and F derivatives. Thus, the invention is further directed to a process for making 13,14-dihydroprostaglandin A, E and F derivatives.

Definitions and Usage of Terms

"Alkyl" is a saturated or unsaturated hydrocarbon chain having 1 to 18 carbon atoms, preferably 1 to 12, more preferably 1 to 6, more preferably still 1 to 4 carbon atoms. Alkyl chains may be straight or branched. Preferred branched alkyl have one or two branches, preferably one branch. Preferred alkyl are saturated. Unsaturated alkyl have one or more double bonds and/or one or more triple bonds. Preferred unsaturated alkyl have one or two double bonds or one triple bond, more preferably one double bond. Alkyl chains may be unsubstituted or substituted with from 1 to about 4 substituents. Preferred alkyl are unsubstituted. Preferred substituted alkyl are mono-, di-, or trisubstituted. Preferred alkyl substituents include halo, hydroxy, aryl (e.g., phenyl, tolyl, alkyloxphenyl, alkyloxycarbonylphenyl, halophenyl), heterocyclyl, and heteroaryl.

"Aromatic ring" is an aromatic hydrocarbon ring system. Aromatic rings are monocyclic or fused bicyclic ring systems. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring. Aromatic rings may be unsubstituted or substituted with from 1 to about 4 substituents on the ring. Preferred aromatic ring substituents include: halo, cyano, alkyl, heteroalkyl, haloalkyl, phenyl, phenoxy or any combination thereof. More preferred substituents include halo and haloalkyl. Preferred aromatic rings include naphthyl and phenyl. The most preferred aromatic ring is phenyl.

"Biohydrolyzable ester" is an ester moiety that does not interfere with the therapeutic activity of the compound, or that is readily metabolized by a human or mammal.

"Carbocyclic aliphatic ring" is a saturated or unsaturated hydrocarbon ring. Carbocyclic aliphatic rings are not aromatic. Carbocyclic aliphatic rings are monocyclic, or are fused, spiro, or bridged bicyclic ring systems. Monocyclic carbocyclic aliphatic rings contain from about 4 to about 10 carbon atoms, preferably from 4 to 7 carbon atoms, and most preferably from 5 to 6 carbon atoms in the ring. Bicyclic carbocyclic aliphatic rings contain from 8 to 12 carbon atoms, preferably from 9 to 10 carbon atoms in the ring. Carbocyclic aliphatic rings may be unsubstituted or substituted with from 1 to about 4 substituents on the ring. Preferred carbocyclic aliphatic ring substituents include: halo, cyano, alkyl, heteroalkyl, haloalkyl, phenyl, phenoxy or any combination thereof. More preferred substituents include halo and haloalkyl. Preferred carbocyclic aliphatic rings include cyclopentyl, cyclohexyl, cyclohexenyl, cycloheptyl, and cyclooctyl. More preferred carbocyclic aliphatic rings include cyclohexyl, cycloheptyl, and cyclooctyl. The most preferred carbocyclic aliphatic ring is cycloheptyl.

"Halo" is fluoro, chloro, bromo or iodo. Preferred halo are fluoro, chloro and bromo; more preferred are chloro and fluoro, especially fluoro.

"Haloalkyl" is a straight, branched, or cyclic hydrocarbon substituted with one or more halo substituents. Preferred haloalkyl are $C_1-C_{12}$; more preferred are $C_1-C_6$; more preferred still are $C_1-C_3$. Preferred halo substituents are fluoro and chloro. The most preferred haloalkyl is trifluoromethyl.

"Heteroalkyl" is a saturated or unsaturated chain containing carbon and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to about 4 substituents. Preferred heteroalkyl are unsubstituted. Preferred heteroalkyl substituents include halo, hydroxy, aryl (e.g., phenyl, tolyl, alkyloxyphenyl, alkyloxycarbonylphenyl, halophenyl), heterocyclyl, heteroaryl. For example, alkyl substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), amino (e.g., amino, mono- and di- $C_1-C_3$ alkanylamino, methylphenylamino, methylbenzylamino, $C_1-C_3$ alkanylamido, carbamamido, ureido, guanidino).

"Heteroatom" is a nitrogen, sulfur, or oxygen atom. Groups containing more than one heteroatom may contain different heteroatoms.

"Heterocyclic aliphatic ring" is a saturated or unsaturated ring containing carbon and from 1 to about 4 heteroatoms in the ring, wherein no two heteroatoms are adjacent in the ring and no carbon in the ring that has a heteroatom attached to it also has a hydroxyl, amino, or thiol group attached to it. Heterocyclic aliphatic rings are not aromatic. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 member atoms in the ring. Bicyclic heterocyclic aliphatic rings contain from 8 to 12 member atoms, preferably 9 or 10 member atoms in the ring. Heterocyclic aliphatic rings may be unsubstituted or substituted with from 1 to about 4 substituents on the ring. Preferred heterocyclic aliphatic ring substituents include: halo, cyano, alkyl, heteroalkyl, haloalkyl, phenyl, phenoxy or any combination thereof. More preferred substituents include halo and haloalkyl. Preferred heterocyclic aliphatic rings include piperzyl, morpholinyl, tetrahydrofuranyl, tetrahydropyranyl and piperdyl.

"Heteroaromatic ring" is an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings contain from 8 to 12 member atoms, preferably 9 or 10 member atoms in the ring. Heteroaromatic rings may be unsubstituted or substituted with from 1 to about 4 substituents on the ring. Preferred heteroaromatic ring substituents include: halo, cyano, alkyl, heteroalkyl, haloalkyl, phenyl, phenoxy or any combination thereof. More preferred substituents include halo, haloalkyl, and phenyl. Preferred heteroaromatic rings include thienyl, thiazolo, purinyl, pyrimidyl, pyridyl, and furanyl. More preferred heteroaromatic rings include thienyl, furanyl, and pyridyl. The most preferred heteroaromatic ring is thienyl.

"Lower alkyl" is an alkyl chain radical comprised of 1 to 6, preferably 1 to 4 carbon atoms.

"Phenyl" is a six-membered monocyclic aromatic ring which may or may not be substituted with from about 1 to about 4 substituents. The substituents may be substituted at the ortho, meta or para position on the phenyl ring, or any combination thereof. Preferred phenyl substituents include: halo, cyano, alkyl, heteroalkyl, haloalkyl, phenyl, phenoxy or any combination thereof. More preferred substituents on the phenyl ring include halo and haloalkyl. The most preferred substituent is halo. The preferred substitution pattern on the phenyl ring is ortho or meta. The most preferred substitution pattern on the phenyl ring is ortho.

The Novel Epoxide Intermediate

The present invention is directed to a process for making a novel Methyl 7-(2-hydroxy-5-(2-(2-oxiranyl)ethyl)-4-(1, 1,2,2 tetramethyl-1-silapropoxy) cyclopentyl) heptanoate intermediate (the "epoxide intermediate") having the following general formula:

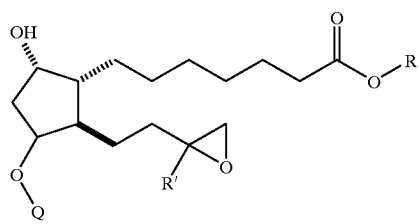

Formula I wherein:

a) R is lower alkyl, carbocyclic aliphatic ring, heterocyclic aliphatic ring, aromatic ring, or heteroaromatic ring;

b) R' is hydrogen, lower alkyl, carbocyclic aliphatic ring, heterocyclic aliphatic ring, aromatic ring, or heteroaromatic ring provided the carbon at $C_{15}$ (prostaglandin numbering) has only one heteroatom attached to it; and c) Q is a suitable protecting group. Suitable protecting groups include tert-butyl dimethylsilyl, trimethylsilyl, benzyl, $C_1$–$C_8$ alkyl, or aromatic ether, or a benzoyl or acetyl ester. Preferred protecting groups include tert-butyl dimethylsilyl, trimethylsilyl, and benzyl ethers. The most preferred protecting group is a tert-butyl dimethylsilyl ether.

Compounds Prepared Using the Present Process

This epoxide intermediate above is useful for making 13,14-dihydro prostaglandin A, E and F derivatives. Thus, the invention is further directed to a process for making 13,14-dihydro prostaglandin A, E and F derivatives having the following general formula:

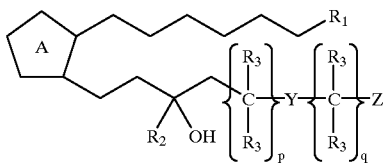

Formula II wherein:

a) $R_1$ is $CO_2H$, $C(O)NHOH$, $CO_2R_5$, $CH_2OH$, $S(O)_2R_5$, $C(O)NHR_5$, $C(O)NHS(O)_2R_5$, or tetrazole; wherein $R_5$ is alkyl, heteroalkyl, carbocyclic aliphatic ring, heterocyclic aliphatic ring, aromatic ring, or heteroaromatic ring;

b) $R_2$ is hydrogen, lower alkyl carbocyclic aliphatic ring, heterocyclic aliphatic ring, aromatic ring, or heteroaromatic ring;

c) each $R_3$ is independently selected from the group consisting of: hydrogen, lower alkyl, alkoxy, haloalkyl, carbocyclic aliphatic ring, heterocyclic aliphatic ring, aromatic ring, and heteroaromatic ring;

d) Y is $NR_4$, S, S(O), $S(O)_2$, O, or a bond wherein $R_4$ is hydrogen or lower alkyl;

e) p is 0–5, q is 0–5, and p+q is 0–5 provided that when Y is a bond p is at least 1;

f) Z is hydrogen, methyl, carbocyclic aliphatic ring, heterocyclic aliphatic ring, aromatic ring, or heteroaromatic ring provided that when Y is $NR_4$, S, S(O), or $S(O)_2$ and q is 0, Z is not hydrogen;

g)

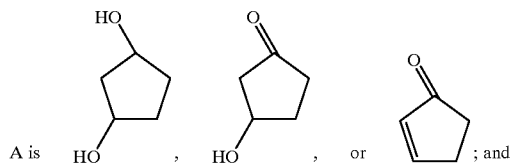

A is , , or ; and h) provided the carbon at $C_{15}$ (prostaglandin numbering) has only one heteroatom attached to it.

The 13,14-dihydro prostaglandin A, E and F derivatives described directly above may themselves be used as intermediates in the preparation of other 13,14-dihydro prostaglandin A, E or F derivatives. That is, the compounds prepared may be reacted further, using known chemistry, to yield other active derivatives, such as other PGA, PGE and PGF derivatives.

Compounds which may be prepared using the process of the present invention include, but are not limited to, those shown below:

13, 14-dihydro-16-(phenylthio)-16-tetranor Prostaglandin $F_1\alpha$ methyl ester:

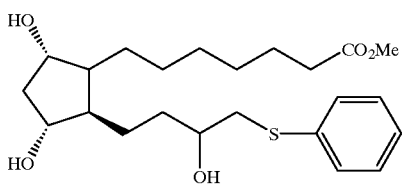

-continued 13,14-dihydro-16-(3-methylphenylthio)-16-tetranor Prostaglandin F$_1$α:

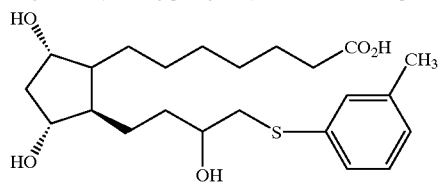

13,14-dihydro-16-(3-trifluoromethylphenylthio)-16-tetranor Prostaglandin F$_1$α methyl ester:

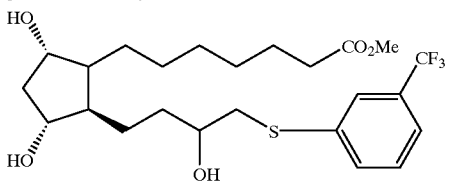

13,14-dihydro-16-(2,3,5,6-tetrafluorophenylthio)-16-tetranor Prostaglandin F$_1$α:

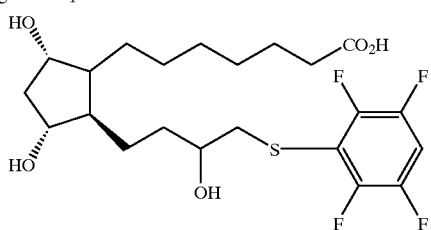

13,14-dihydro-16-(2-methylphenylthio)-16-tetranor Prostaglandin F$_1$α methyl ester:

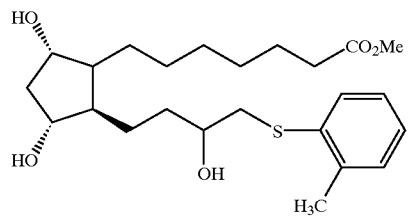

13,14-dihydro-16-(4-methylphenylthio)-16-tetranor Prostaglandin F$_1$α:

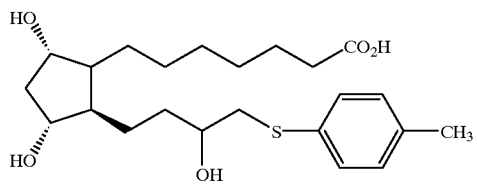

13,14-dihydro-16-(2-fluorophenylthio)-16-tetranor Prostaglandin F$_1$α methyl ester:

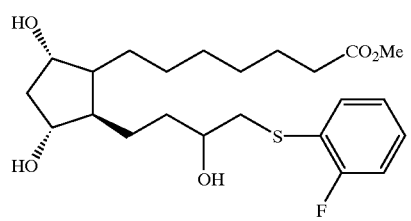

-continued 13,14-dihydro-15-methyl-16-(phenylthio)-16-tetranor Prostaglandin F$_1$α methyl ester:

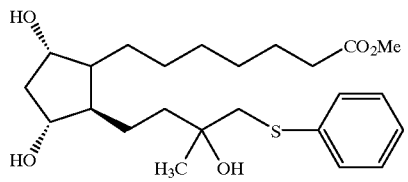

13,14-dihydro-15-methyl-16-(2-methylphenylthio)-16-tetranor Prostaglandin F$_1$α methyl ester:

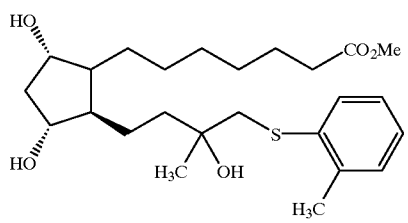

13,14-dihydro-16-(2-thienylthio)-16-tetranor prostaglandin F$_1$α methyl ester:

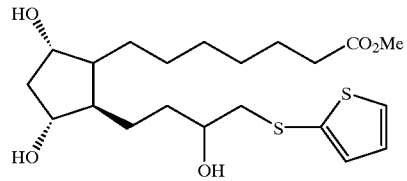

13,14-dihydro-16-(2-methylphenylamino)-16-tetranor prostaglandin F$_1$α:

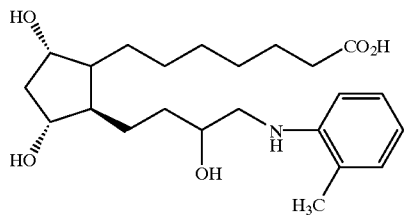

13,14-dihydro-16-(2-fluorophenylamino)-16-tetranor prostaglandin F$_1$α:

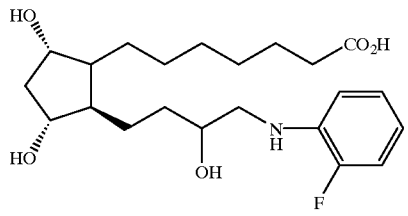

13,14-dihydro-17-(2-fluorophenyl) 17-trinor prostaglandin F$_1$α:

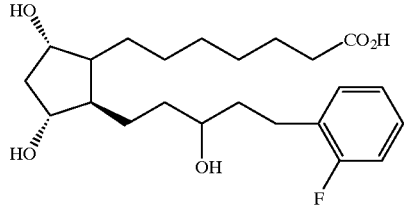

13, 14-dihydro-16-(2-fluorophenoxy)-16-tetranor prostaglandin F$_1\alpha$:

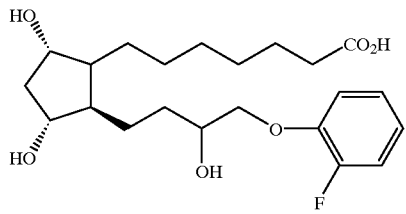

13, 14-dihydro-16-(2,4-dichlorophenoxy)-16-tetranor prostaglandin F$_1\alpha$:

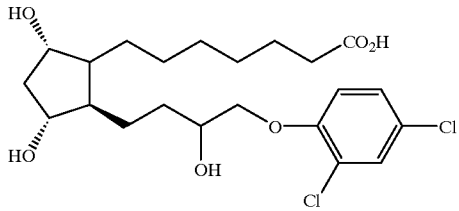

13, 14-dihydro-16-(2-fluorophenylthio)-16-tetranor Prostaglandin F$_1\alpha$ 1-hydroxamic acid:

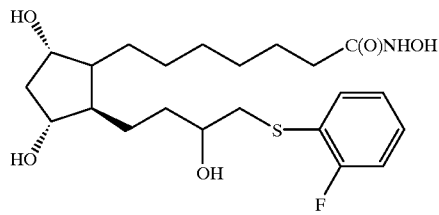

13, 14-dihydro-16-(3-chlorophenylamino)-16-tetranor Prostaglandin F$_1\alpha$ 1-hydroxamic acid:

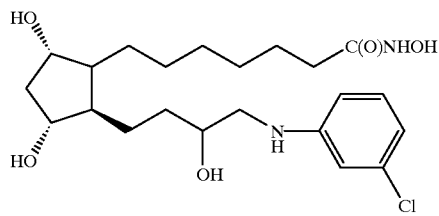

13, 14-dihydro-15-methyl-16-(2-methylphenylthio)-16-tetranor Prostaglandin F$_1\alpha$ 1-N-methanesulfonamide:

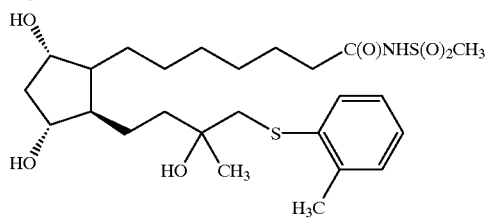

13, 14-dihydro-16-(phenylthio)-16-tetranor prostaglandin E$_1$:

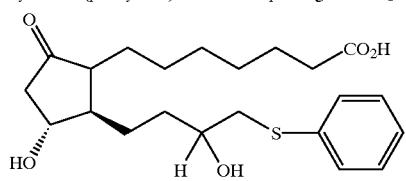

13, 14-dihydro-16-(phenylthio)-16-tetranor Prostaglandin E$_1$ methyl ester:

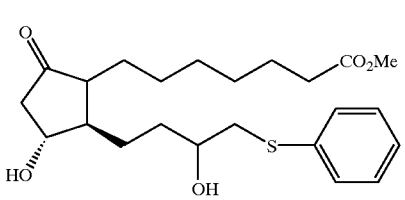

13, 14-dihydro-16-(3-methylphenylthio)-16-tetranor Prostaglandin E$_1$:

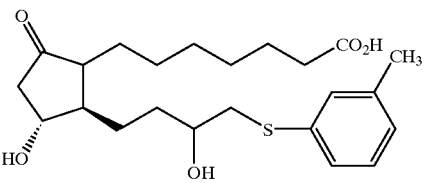

13, 14-dihydro-16-(3-trifluoromethylphenylthio)-16-tetranor Prostaglandin E$_1$ methyl ester:

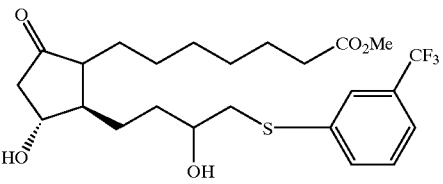

13, 14-dihydro-16-(2, 3, 5, 6-tetrafluorophenylthio)-16-tetranor Prostaglandin E$_1$:

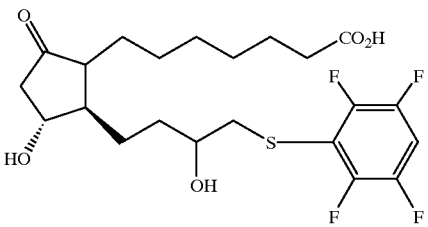

13, 14-dihydro-16-(2-methylphenylthio)-16-tetranor Prostaglandin E$_1$ methyl ester:

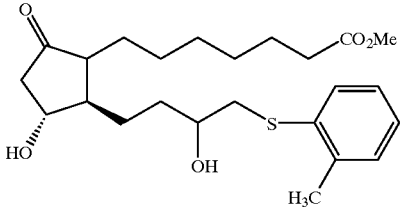

13, 14-dihydro-16-(4-methylphenylthio)-16-tetranor Prostaglandin E$_1$:

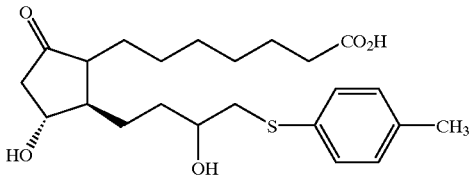

13,14-dihydro-16-(2-fluorophenylthio)-16-tetranor Prostaglandin E₁ methyl ester:

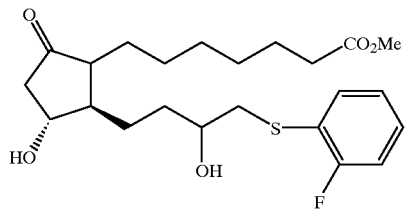

13,14-dihydro-15-methyl-16-(phenylthio)-16-tetranor Prostaglandin E₁ methyl ester:

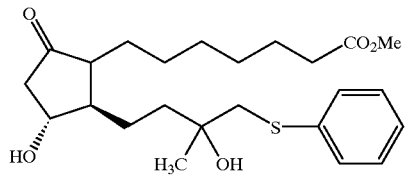

13,14-dihydro-16-(2-thienylthio)-16-tetranor prostaglandin E₁ methyl ester:

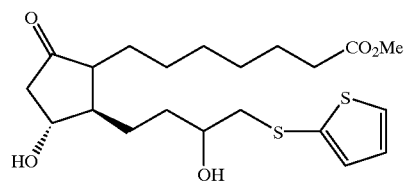

13,14-dihydro-16-(2-methylphenylamino)-16-tetranor prostaglandin E₁:

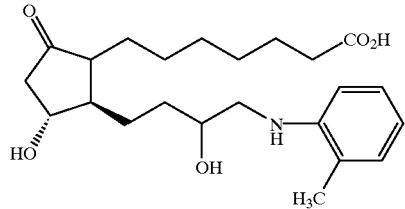

13,14-dihydro-16-(2-fluorophenylamino)-16-tetranor prostaglandin E₁:

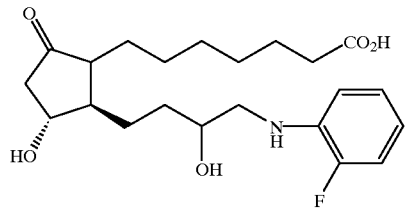

13,14-dihydro-16-(phenylthio)-16-tetranor prostaglandin A₁:

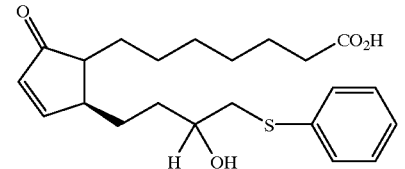

13,14-dihydro-16-(3-trifluoromethylphenylthio)-16-tetranor Prostaglandin A₁ methyl ester:

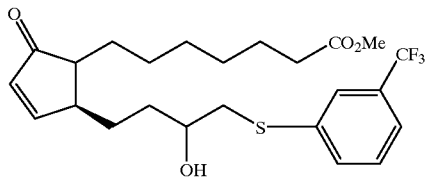

13,14-dihydro-16-(2,3,5,6-tetrafluorophenylthio)-16-tetranor Prostaglandin A₁:

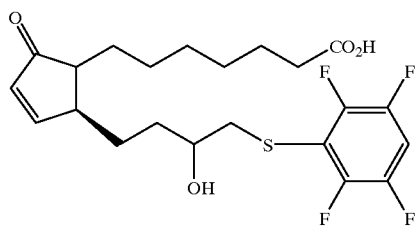

13,14-dihydro-16-(2-methylphenylthio)-16-tetranor Prostaglandin A₁ methyl ester:

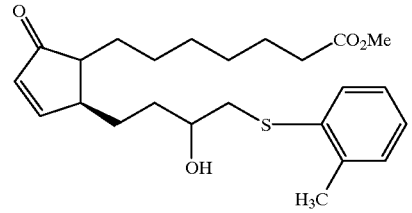

13,14-dihydro-16-(4-methylphenylthio)-16-tetranor Prostaglandin A₁:

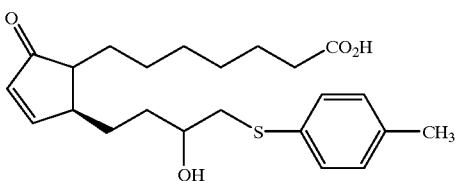

13,14-dihydro-16-(2-fluorophenylthio)-16-tetranor Prostaglandin A₁ methyl ester:

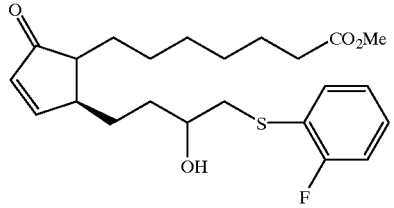

13,14-dihydro-15-methyl-16-(phenylthio)-16-tetranor Prostaglandin A₁ methyl ester:

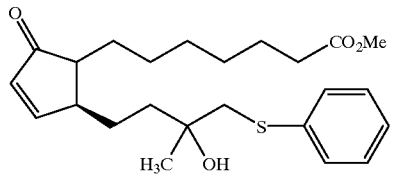

13,14-dihydro-16-(2-thienylthio)-16-tetranor prostaglandin A₁ methyl ester:

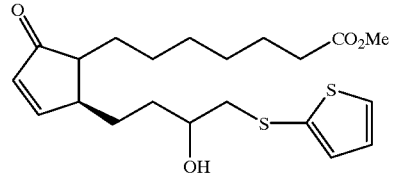

13,14-dihydro-16-(2-methylphenylamino)-16-tetranor prostaglandin $A_1$

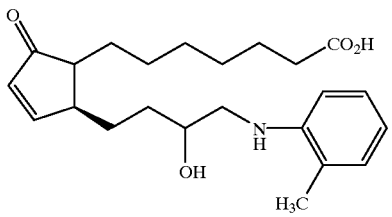

13,14-dihydro-16-(3-chlorophenylamino)-16-tetranor Prostaglandin $A_1$ 1-hydroxamic acid:

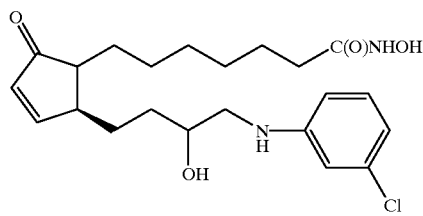

Process for Making the Novel Epoxide Intermediate

The process for making the novel epoxide intermediates according to Formula I above is depicted below in the following general reaction scheme:

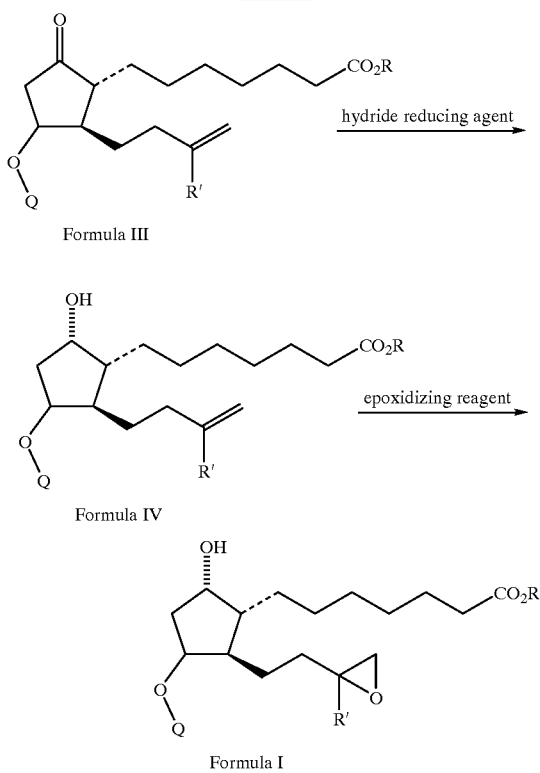

The process depicted above in Scheme I begins with providing a compound according to Formula III. Compounds according to Formula III can be made from known starting materials and methods known to those skilled in the art. For example, the commercially available material Methyl 7-[3-(R)-hydroxy-5-oxo-1-cyclopent-1-yl] heptanoate (Cayman Chemical) can be modified according to processes exemplified by the following references: House, H. O.; Chu, C. Y.; Wilkins, J. M.; Umen, M. J. "The Chemistry of Carbanions. XXVII. A Convenient Precursor for the Generation of Lithium Organocuprates" J. Org. Chem. 1975, 40(10), p. 1460–1468.; 2) Knochel, P.; Jeong, N.; Rozema, M. J.; Yeh, M. C. P.: "Zinc and Copper Carbenoids as Efficient and Selective $a^1/d^1$ Multicoupling Reagents" J. Amer. Chem. Soc. 1989, 111, p. 6474–6476. A particularly preferred method for preparing such compounds is described below in Example I.

The next step in the process is modifying the compound according to Formula III to yield a compound according to Formula IV. The compound according to Formula III is treated with a hydride reducing agent, such as those reported in the art for PGF derivatives (see for example Davis et al., "A Convergent Total Synthesis of (+-)-Prostaglandin $F_{2\alpha}$ via Conjugate Addition and Regiospecific Enolate Trapping" J. Org. Chem. 1979, 44(22), p.3755–3759). The ketone is reacted with a hydride reducing agent in a polar protic solvent to give the $C_9$ alcohol. "Hydride reducing agent" refers to any agent capable of delivering a hydride ion in a reaction. Preferred hydride reducing agents include L-selectride and sodium borohydride. The most preferred hydride reducing agent is sodium borohydride. Preferred polar protic solvents include methanol, ethanol, and butanol. The most preferred polar protic solvent is methanol. The preferred temperature range for the reduction is between −100° C. and 23° C. More preferred still is between −60° C. and 0° C. The most preferred temperature range is between −45° C. and −20° C.

The product alcohol so obtained can be isolated using methods known to those skilled in the art. Such methods include extraction, solvent evaporation, distillation, and crystallization procedures. Most preferably, the product is purified by flash chromatography on silica gel (Merck, 230–400 mesh) using 20% EtOAc/hexanes as the eluent.

Finally, the compound according to Formula IV is then treated with an epoxidizing agent in a halocarbon solvent to provide a novel epoxide intermediate according to Formula I. "Epoxidizing agent" refers to a chemical capable of producing a 3-membered ring possessing one oxygen atom from a carbon—carbon double bond. Preferred epoxidizing agents include meta-chloroperbenzoic acid and peracetic acid. More preferred epoxidizing agents include meta-chloroperbenzoic acid and peracetic acid. The most preferred epoxidizing agent is meta-chloroperbenzoic acid. "Halocarbon solvent" refers to a solvent which has one or more halogens attached to a carbon chain. Preferred halocarbon solvents include dichloromethane, dichloroethane, carbon tetrachloride, and chloroform. More preferred halocarbon solvents include dichloromethane and chloroform. The most preferred halocarbon solvent is dichloromethane.

The epoxide intermediates according to Formula I can be isolated using methods known to those skilled in the art. Such methods include extraction, solvent evaporation, distillation, or crystallization procedures. Most preferably, the product is purified by flash chromatography on silica gel (Merck, 230–400 mesh) using 20% EtOAc/hexanes as the eluent.

Process for Making 13,14-dihydro prostaglandin A, E, and F Derivatives

The process for making the 13,14-dihydro prostaglandin A, E, and F derivatives according to Formula II above is depicted below in the following general reaction scheme:

Scheme II

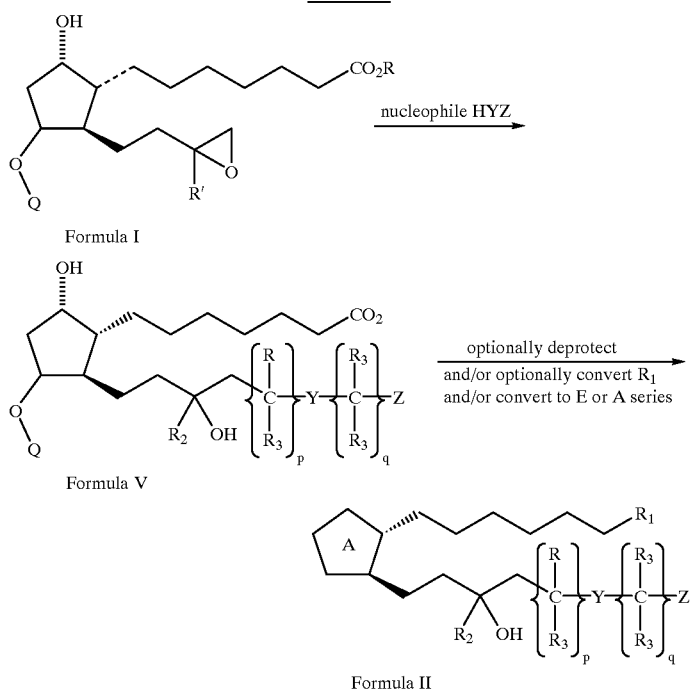

Formula I

Formula V

Formula II

The novel epoxide intermediates according to Formula I can be reacted with a variety of carbon, oxygen, sulfur and nitrogen containing nucleophiles ("nucleophile HYZ") as described in the art to provide $C_{11}$-protected 13,14-dihydro-15-substituted-16-substituted tetranor prostaglandin A, E, and F derivatives (see for example: Smith, J. G., "Synthetically Useful Reactions of Epoxides", *Synthesis* 1984, p.629–656). "Nucleophile HYZ" refers to any chemical agent suitable for adding to an epoxide to form a covalent bond in a ring-opening process. Preferred nucleophiles include 2-thienyl mercaptan, o,m,p-chlorophenol, ethyl mercaptan, o,m,p-lithio chlorobenzene, morpholine, thiophenol, aniline, o,m,p-toluidine, o,m,p-chloro thiophenol, o,m,p-fluoro thiophenol, o,o-dichloro thiophenol, phenylurethane, o,m,p-trifluoromethyl thiophenol, furfuryl amine, benzyl amine, furfuryl alcohol, and 2-amino pyridine. More preferred nucleophiles include thiophenol, o-chloro thiophenol, and aniline. The most preferred nucleophile is o-F-thiophenol.

Deprotection at $C_{11}$ can then be carried out when the compound according to Formula I is intended to be a PGF derivative. "Deprotection" refers to the removal of protecting groups used to protect sensitive functional groups. Deprotection includes the removal of silyl ethers of alcohols or alkyl esters of carboxylic acids.

Conversion of the R ester of the Formula V compound to the desired $R_1$ of Formula II can be carried out using methods known to those skilled in the art. Such methods include, but are not limited to, deprotection of $C_{11}$, deprotection of $C_1$, selective oxidation of $C_9$, reduction of $C_1$, base catalyzed elimination of the $C_{11}$, alcohol, condensation of $C_1$ with amines, and condensation of $C_1$ with hydroxylamines.

Conversion to a PGE derivative from the corresponding PGF derivative according to Formula II can be carried out by oxidization at $C_9$ using methods known to those skilled in the art. Conversion to a PGA derivative from the corresponding PGE derivative can be carried out by elimination of the $C_{11}$ alcohol using methods known to those skilled in the art.

Addition of sulfur and oxygen nucleophiles is carried out in the presence of base. "Base" means a basic reagent which is added to the reaction mixture to facilitate covalent bond formation and ring-opening of the epoxide and the nucleophile. Bases include nitrogen bases. Preferred bases include those which are soluble in organic solvents and are volatile. Specifically, preferred bases include N,N diisopropylethylamine, triethylamine, trimethylamine, butylamine, pyridine, and 2,6-lutidine. The more preferred bases are 2,6-lutidine, triethylamine, and pyridine. The most preferred base is triethylamine. The reaction is carried out preferably at between 150° C. and 0° C., more preferably between 120° C. and 20° C. and most preferably between 80° C. and 50° C. The preferred organic solvents for the reaction are aromatic hydrocarbon solvents. More preferred organic solvents include xylenes, toluene, and benzene. The most preferred organic solvent is benzene.

Addition of nitrogen nucleophiles is carried out in the presence of a Lewis acid and a polar aprotic solvent or with no solvent. "Lewis acid" refers to any non-protic acid which is added to the reaction mixture to facilitate covalent bond formation and ring-opening of the epoxide with the nucleophile. The preferred Lewis acids include magnesium perchlorate, boron trifluoride etherate, titanium tetrachloride and triethylaluminum. The most preferred Lewis acid is magnesium perchlorate. Polar aprotic acids include N,N dimethylformamide and ethereal solvents. "Ethereal solvent" refers to a solvent which has two alkyl groups bonded to an oxygen including those in which the alkyl group and oxygen are part of a ring. Preferred ethereal solvents include diethyl ether and tetrahydrofuran. The most preferred ethereal solvent is tetrahydrofuran. The most preferred polar aprotic solvent is N,N dimethylformamide. The preferred reaction temperature is between 150° C. and 23° C. The more preferred reaction temperature is between 125° C. and 40° C. The most preferred temperature is between 100° C. and 75° C.

Addition of carbon nucleophiles generated from the anion is carried out in the presence of a Lewis acid and an ethereal solvent. Preferred ethereal solvents include diethyl ether and tetrahydrofuran. The most preferred ethereal solvent is tetrahydrofuran. The most preferred Lewis acid with carbon nucleophiles is boron trifluoride-etherate.

The following non-limiting examples illustrate the processes of the present invention:

EXAMPLE 1

Preparation of Formula III Compounds:

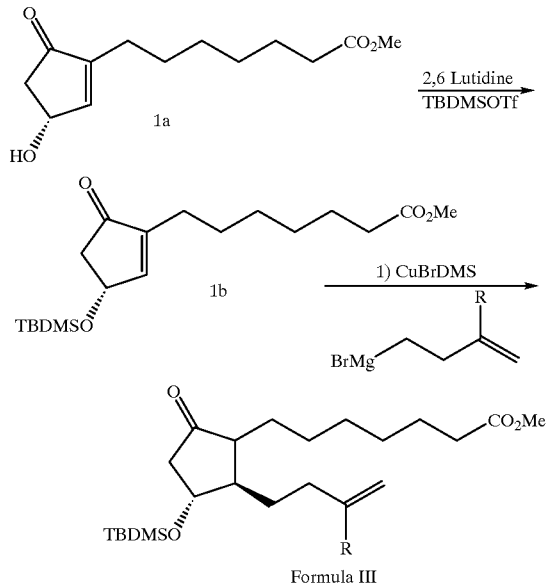

Formula III

Methyl 7-(2-oxo-4-(1,1,2,2-tetramethyl-1-silapropoxy) cyclopent-1-enyl) heptanoate 1b:

To a solution of Methyl-7-[3-(R)-hydroxy-5-oxo-1-cyclopenten-1-yl] heptanoate 1a (1 equiv.) in $CH_2Cl_2$ at −78° C. is added 2,6 Lutidine (1.3 equiv.) dropwise over 15 minutes. The solution is kept at −78° C. and TBDMS Triflate (1.2 equiv.) in $CH_2Cl_2$ is added dropwise over 15 minutes. The reaction is warmed gradually to room temperature and stirred at room temperature for 15 hours. Aqueous 10% HCl is added and the layers are separated. The water layer is extracted with $CH_2Cl_2$ and the organic layers are combined. The organic layer is washed with brine, dried ($Na_2SO_4$) and concentrated. The residue is distilled under vacuum (house vacuum, 10 mm Hg) to provide 89% of the silyl ether 1b.

Compounds according to Formula III

To a slurry of $Mg^0$ powder (2 equiv.) in THF at room temperature is added one crystal of $I_2$ and the appropriate bromide (2equiv.) dropwise over 10 minutes. Preferred bromides include 1-bromobutene, 1-bromo-3-methylbutene, and 1-bromo-3-ethylbutene. The reaction exotherms as the addition continues. After the addition is complete, the reaction is refluxed for 3 hours and cooled to room temperature. The Grignard is diluted with THF and added via cannula to a 3-necked flask equipped with mechanical stirring and charged with CuBr.DMS (2 equiv.) in a 1:1 solution of THF/DMS at −78° C. After the addition of the Grignard (~20 min), the reaction is stirred 1 hour at −78° C. The color of the reaction is dark red at this point. A solution of the ketone 1b (1 equiv.) in THF is then added dropwise over 25 minutes. The reaction is stirred at −78° C. for 15 minutes, then allowed to warm slowly to room temperature over 2 hours. The reaction is quenched with aq. $NH_4Cl$ and the excess DMS allowed to evaporate overnight. The reaction is partitioned between brine/$CH_2Cl_2$ and the layers separated. The aqueous layer is back-extracted with $CH_2Cl_2$ and the organic layers are combined and dried ($Na_2SO_4$). The solvent is removed in vacuo and the residue chromatographed on $SiO2$ (10% hexane/EtOAc) to give 71% of the appropriate ketone according to Formula III.

EXAMPLE 2

Preparation of Methyl 7-(2-hydroxy-5-(2-(2-oxiranyl)ethyl-4-(1,1,2,2-tetramethyl-1 silapropoxy)cyclopentyl)heptanoate 2c

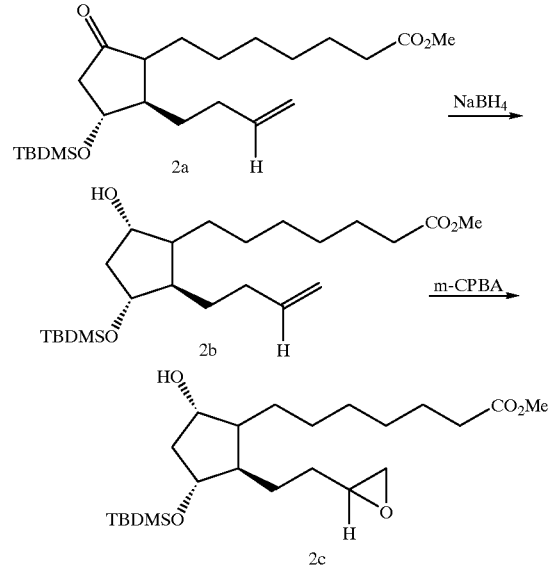

The ketone 2a (1 equiv.) is dissolved in MeOH and cooled to −40° C. Sodium borohydride (0.9 equiv.) is added portionwise over 10 minutes. After the addition is complete the reaction is stirred for 13 hours at −40° C. and then 12 hours at −78° C. The reaction is quenched with water, partitioned between brine and $CH_2Cl_2$ and the layers separated. The aqueous layer is back-extracted with $CH_2Cl_2$ and the organic layers combined and dried ($Na_2SO_4$). The solvent is removed in vacuo and the residue chromatographed on $SiO_2$ (30% EtOAc/hexanes) to give 75% of the alcohol 2b.

The alcohol 2b (1 equiv.) is dissolved in $CH_2Cl_2$ and cooled to 0° C. Sodium bicarbonate is added, followed by m-CPBA (57%–85% purity) (3 equiv.) portionwise over 15 minutes. After the addition is complete the reaction is stirred for 20 hours at room temperature. The reaction is poured onto water, partitioned between brine and $CH_2Cl_2$ and the layers separated. The aqueous layer is back-extracted with $CH_2Cl_2$ and the organic layers combined and dried ($Na_2SO_4$). The solvent is removed in vacuo and the residue chromatographed on $SiO_2$ (20% EtOAc/hexanes) to give 73% of the epoxide diasteriomers 2c.

EXAMPLE 3

Preparation of 13,14-dihydro-16-(phenylthio)-16-tetranor prostaglandin $F_1\alpha$ methyl ester 3a:

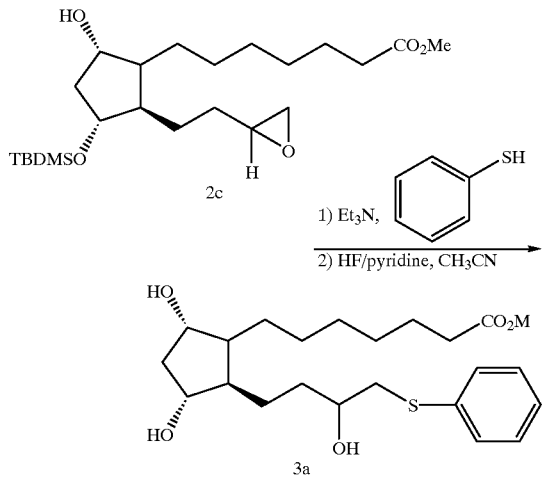

In a 5 ml round bottomed flask epoxide 2c (1 equiv.) and dry benzene are added. The flask is cooled to 0° C., then is treated with thiophenol (1.2 equiv.) and triethyl amine (1.2 equiv.). The ice bath is removed and the reaction stirred at room temperature under nitrogen over night. TLC is used to monitor the reaction. An excess amount of thiophenol is added if necessary. The reaction is quenched with brine, and extracted with methylene chloride, The organic layer is washed three times with 1N HCl, brine, dried (Na2SO4), and concentrated. Without further purification, to this crude reaction mixture, $CH_3CN$ and HF/Pyridine are added while the flask is kept at 0° C., After 3 hours at 0° C., the reaction is quenched with saturated NaCl. The aqueous layer is extracted three times with $CH_2Cl_2$, the organic layers are combined and washed three time with 1N HCl, brine, dried (Na2SO4) and concentrated. After column (7:3, Hexane: Ethyl Acetate) 63% of 3a is obtained.

EXAMPLE 4

Preparation of 13,14-dihydro-16-(phenylthio)-16-tetranor prostaglandin $F_1\alpha$ 4a:

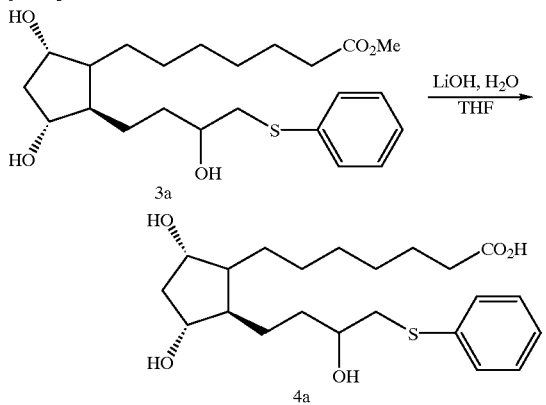

To a 5 ml round bottomed flask, 13,14-dihydro-16-(phenylthio)-16-tetranor Prostaglandin $F_1\alpha$ methyl ester and THF/water solution (3:1, THF:$H_2O$) are added, the flask is cooled at 0° C., then an excess (2.5 eg) amount of lithium hydroxide is added. The ice bath is removed, and the reaction stirred at room temperature over night. Methylene chloride and saturated citric acid are added to the reaction mixture, the aqueous layer is washed 3 times with methylene chloride, the organic layers are combined and are washed with brine, dried ($Na_2SO_4$), and chromatographed (methylene chloride, methanol, acetic acid, 9.6, 0.4, 0.015), 4a is recovered in 63% yield.

EXAMPLE 5

Preparation of 13,14-dihydro-16-(phenylamino)-16-tetranor prostaglandin $F_1\alpha$ methyl ester:

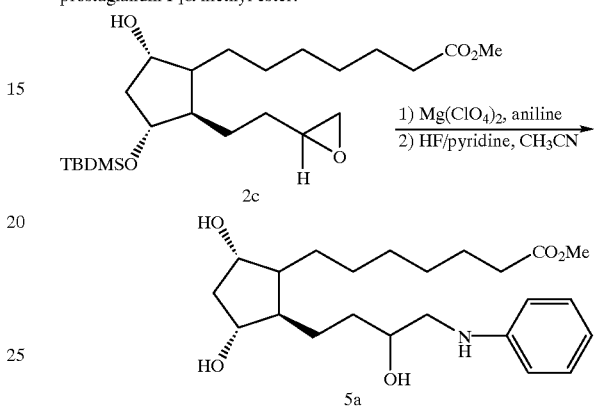

To a 10 ml round bottomed flask epoxide 2c (1 equiv.), aniline (1.5 equiv.), catalytic magnesium perchlorate, and THF are added. After the reaction is refluxed under nitrogen overnight, the reaction is done. The flask is cooled to room temperature, and the solvent removed in vacuo. Without further purification to this crude reaction mixture, $CH_3CN$ and HF/Pyridine (0.6 equiv.) are added while the flask is kept at 0° C. After 5 hours at 0° C., the reaction is quenched with saturated NaCl. The aqueous layer is extracted three times with $CH_2Cl_2$, the organic layers are combined and washed three time with saturated $NaHCO_3$, brine, and dried ($Na_2SO_4$). After column (95% $CH_2Cl_2$, 5% MeOH) 5a is recovered in 50% yield.

EXAMPLE 6

Preparation of 13,14-dihydro-16-(phenylthio)-16-tetranor Prostaglandin $F_1\alpha$ 1-hydroxamic acid:

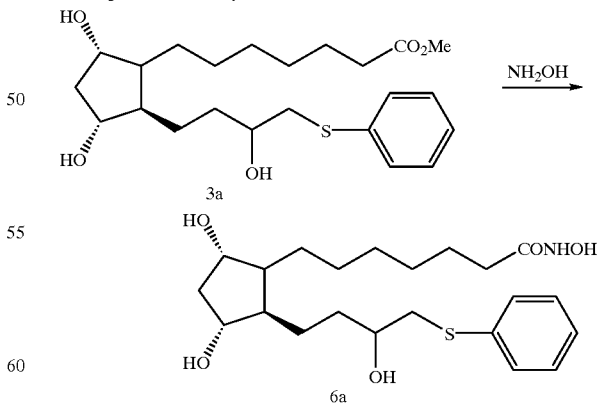

In a flame-dried 25 mL round-bottomed flask equipped with a magnetic stir bar is placed 13,14-dihydro-16-(phenylthio)-16-tetranor Prostaglandin $F_{1\alpha}$ methyl ester 3a (1.0 equiv.) in methanol. To this solution is added hydroxylamine in methanol (1.25 equiv.). The solution stirred for 18 hours. The solution is then treated with 1N hydrochloric acid and extracted with ethyl acetate. The organic layer is washed with brine, dried over anhydrous MgSO4, filtered and concentrated under reduced pressure. The residue is purified by chromatography to give 13,14-dihydro-16-(phenylthio)-16-tetranor Prostaglandin $F_1\alpha$ 1-hydroxamic acid 6a.

EXAMPLE 7

Preparation of 13,14-dihydro-17-(2-methylphenyl) 17-trinor prostaglandin $F_1\alpha$

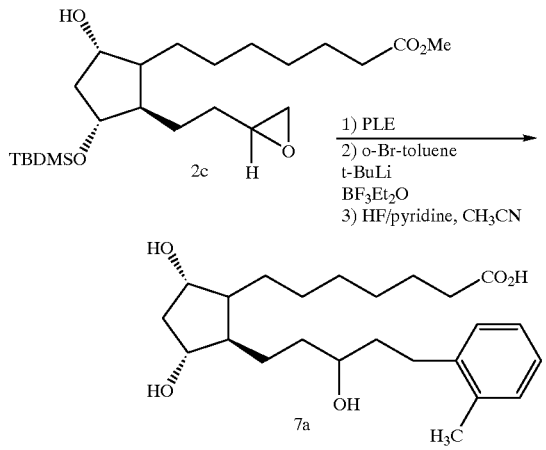

The epoxide 2c is treated with pig liver esterase to remove the methyl ester. Then, to a 10 ml round bottomed flask at −78° C., the acid and $BF_3Et_2O$ are stirred, then the lithio anion of o-bromotoluene(1.5 equiv.), in THF are added. After the reaction is stirred at −30° C. under nitrogen for several hours, the reaction is done. The reaction is quenched with saturated $NH_4Cl$, and the solvent removed in vacuo. Without further purification to this crude reaction mixture, $CH_3CN$ and HF/Pyridine (0.6 equiv.) are added while the flask is kept at 0° C. After 5 hours at 0° C., the reaction is quenched with saturated NaCl. The aqueous layer is extracted three times with $CH_2Cl_2$, the organic layers are combined and washed three time with saturated $NaHCO_3$, brine, and dried ($Na_2SO_4$). After column (95% $CH_2Cl_2$, 5% MeOH) of product 7a is recovered in 50% yield.

What is claimed:

1. A method of preparing a compound having the structure:

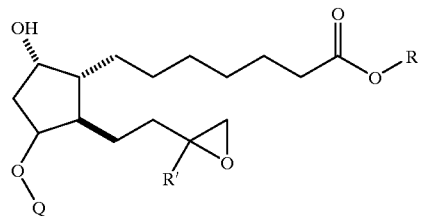

wherein

R is lower alkyl, carbocyclic aliphatic ring, heterocyclic aliphatic ring, aromatic ring, or heteroaromatic ring;

R' is hydrogen, lower alkyl, carbocyclic aliphatic ring, heterocyclic aliphatic ring, aromatic ring, or heteroaromatic ring provided the carbon at $C_{15}$ (prostaglandin numbering) has only one heteroatom attached to it; and Q is a suitable protecting group, comprising the steps of:

a) providing a compound having the structure:

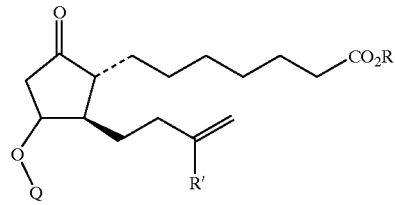

wherein

R is lower alkyl, carbocyclic aliphatic ring, heterocyclic aliphatic ring, aromatic ring, or heteroaromatic ring;

R' is hydrogen, lower alkyl, carbocyclic aliphatic ring, heterocyclic aliphatic ring, aromatic ring, or heteroaromatic ring provided the carbon at $C_{15}$ (prostaglandin numbering) has only one heteroatom attached to it; and Q is a suitable protecting group;

b) adding a hydride reducing agent to the compound provided in step a; and c) adding an epoxidizing agent to the product of step b.

2. The method of claim 1 wherein the hydride reducing agent is selected from the group consisting of L-selectride and sodium borohydride.

3. The method of claim 2 wherein the epoxidizing agent is selected from the group consisting of meta-chloroperbenzoic acid and peracetic acid.

4. The method of claim 3 wherein the hydride reducing agent is sodium borohydride and the epoxidizing agent is meta-chloroperbenzoic acid.

5. The method of claim 4 wherein the step of adding a hydride reducing agent is carried out in a temperature range from −45° C. to −20° C.

6. A compound having the structure:

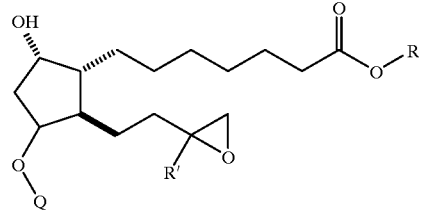

wherein a) R is lower alkyl, carbocyclic aliphatic ring, heterocyclic aliphatic ring, aromatic ring, or heteroaromatic ring;

b) R' is hydrogen, lower alkyl, carbocyclic aliphatic ring, heterocyclic aliphatic ring, aromatic ring, or heteroaromatic ring provided the carbon at $C_{15}$ (prostaglandin numbering) has only one heteroatom attached to it; and c) Q is a suitable protecting group.

7. The compound of claim 6 wherein R is methyl and Q is tert-butyl dimethyl silyl.

8. The compound of claim 7 wherein R' is H.

9. The method of claim 1 wherein R is $CH_3$.

10. The method of claim 9 wherein R' is H.

11. The method of claim 10 wherein Q is tert-butyl-dimethylsilyl.

12. The method of claim 3 wherein R is $CH_3$.

13. The method of claim 12 wherein R' is H.

14. The method of claim 13 wherein Q is tert-butyl-dimethylsilyl.

* * * * *